United States Patent [19]
Howell et al.

[11] Patent Number: 5,597,798
[45] Date of Patent: Jan. 28, 1997

[54] TAXOL AND EPIDERMAL GROWTH FACTOR USED TO ENHANCE TREATMENT OF OVARIAN CANCER

[75] Inventors: Stephen B. Howell, Del Mar; Randolph D. Christen, San Diego, both of Calif.; Seiji Isonishi, Suginami-Ku, Japan; Paul A. Andrews, Washington Grove, Md.

[73] Assignee: The Regents of the University of California, Oakland, Calif.

[21] Appl. No.: 212,110

[22] Filed: Mar. 11, 1994

Related U.S. Application Data

[63] Continuation-in-part of Ser. No. 100,510, Jul. 30, 1993, abandoned, which is a continuation of Ser. No. 488,199, Mar. 5, 1990, Pat. No. 5,252,342.

[51] Int. Cl.[6] .......................... A61K 37/00; A61K 31/225
[52] U.S. Cl. ................................ 514/12; 514/449
[58] Field of Search ..................... 424/9; 514/10, 514/12, 449

[56] References Cited

U.S. PATENT DOCUMENTS

| | | | |
|---|---|---|---|
| 4,571,336 | 2/1986 | Houck et al. | 424/95 |
| 4,863,902 | 9/1989 | Amagase et al. | 514/12 |
| 4,925,922 | 5/1990 | Byers et al. | 530/391 |
| 4,959,353 | 9/1990 | Brown et al. | 514/12 |
| 4,962,091 | 10/1990 | Eppstein et al. | 514/2 |
| 5,252,342 | 10/1993 | Howell et al. | 424/649 |

OTHER PUBLICATIONS

Bil'din, et al., "Participation of the epirmal growth factor and insulin in the regulation of repair gamma–induced DNA single–strand breaks", *Chem. Abs.*, 106(21):169447(u) (1987).

Myers et al., "Conjugates containing tumor–specific agents, cytotoxic agents and biodegradable polymeric carriers for selective delivery of cytotoxic drugs to tumor cells and methods of destroying tumor cells using the conjugates", *Chem. Abs.*, 109(25):222460 (h). (1989).

Aboud–Pirak, et al., "Efficacy of antibodies to epidermal growth factor receptor against KB carcinoma in vitro and n nude mice", *Chem. Abs.*, 110(9):69068(k) (1984).

Hirata, et al., "Possible contribution of protein kinase C activation to priming for DNA synthesis induced by epidermal growth factor with insulin and its inhibition by plasma membrane in primary cultured rat hepatocytes", *Chem. Abs.*, 113(21):185362(n) (1990).

Christen, et al., "Epidermal Growth Factor Regulates the In vitro Sensitivity of Human Ovarian Carcinoma Cells To Cisplatin", *J. Clin. Invest.*, 86:1632–1640 (1990).

Aboud–Pirak, et al., "Efficacy of Antibodies to Epidermal Growth Factor Receptor Against KB Carcinoma In Vitro and in Nude Mice", *Articles*, 80(20):1605–1611 (1988).

*Primary Examiner*—T. J. Criares
*Attorney, Agent, or Firm*—Walter H. Dreger

[57] ABSTRACT

The present invention comprises a method of sensitizing various types of cancer cells derived from different tissues of origin to various cytotoxic agents and augmenting the sensitivity of cancer cells to these cytotoxic agents. The invention provides a method to treat cancer and other cell proliferative diseases by the administration of a sensitizing agent prior to or concurrently with the administration of a cytotoxic agent.

1 Claim, 9 Drawing Sheets

TAXOL AND EPIDERMAL GROWTH FACTOR USED TO ENHANCE TREATMENT OF OVARIAN CANCER

RELATED APPLICATIONS

This application is a continuation-in-part of application Ser. No. 08/100,510, filed 30 Jul. 1993, abandoned, which is a continuation of application Ser. No. 07/488,199, filed 5 Mar. 1990, now U.S. Pat. No. 5,252,342.

FIELD OF THE INVENTION

This invention relates to cancer treatment and to augmentation of anti-neoplastic drug efficacy.

BACKGROUND OF THE INVENTION

Cisplatin (DDP) is one of the most widely used antineoplastic agents for the treatment of human ovarian cancer (Ozois and Young, *Semin. Oncol.* 11:251–263 (1984); Hakes, et al., *Proc. Am. Sci. Clin. Oncol.* 8:152 (1989)). In spite of its potency, the frequent development of DDP resistance is a major obstacle to curative therapy (Chu, et al., *Proc. Am. Assoc. Cancer Res.* 30:594 (1989); Meitner, et al., *Proc. Am. Assoc., Cancer Res.* 30:508 (1989)). Although the mechanism of DDP resistance in vivo is not characterized, a good deal of information is available about mechanisms in cell lines. Impairment of DDP uptake is one of the important mechanisms contributing to DDP resistance (Andrews, et al., *Cancer Res.* 48:68–73 (1988); Waud, *Cancer Res.* 47:6549–655 (1987); Richon, et al., *Cancer Res.* 47:2056–2061 (1987); Teicher, et al., *Cancer Res.* 47:388–393 (1987)). Increased levels of metallothioneins have also been reported in some (Kelley, et al., *Science* 241:1813–1815 (1988)), but not all (Andrews, et al., *Cancer Chemother. Pharmacol.* 19:149–154 (1987)), DDP-resistant cells. Kelley et al. reported that, in a murine leukemia cell line, the degree of resistance was proportional to metallothionein content, and that loss of resistance to DDP in a revertant cell line was associated with concomitant lowering of metallothionein content. Modulation of glutathione (GSH) concentrations in mammalian cells has also been reported to influence the cytotoxicity in DDP (Lee, et al., *Cancer Res.* 48:3661–3665 (1988)). Some DDP-resistant cell lines contain increased amounts of glutathione (Rice, et al., *Cancer Res.* 46:6105–6110 (1986)), and DDP sensitivity can be enhanced under some conditions by extensive depletion of glutathione by buthionine sulfoximine (Andrews, et al., *Mot. Pharmacol.* 30:643–650 (1986)). DDP reacts with DNA to produce an intra-strand N7d(GpG) diamine platinum adduct which comprises 40–60% of the platinum bound to DNA (Poivier, et al., *Proc. Natl. Acad. Sci. U.S.A.* 79:6443–6447 (1982)). DNA repair defective cells are hypersensitive to DDP (Fox and Roberts, *Cancer Metastasis Rev.* 6:261–281 (1987)), and enhanced DNA repair has been implicated in the DDP-resistant phenotype (Masuda, et al., *Cancer Res.* 48:5713–5716 (1988)).

Besides cisplatin, other chemotherapeutic agents exist, including such compounds as carboplatin, tetraplatin, taxol, melphalan, and 5-fluorouracil, all of which exhibit severe toxic side effects that limit somewhat their clinical usefulness. These additional agents exhibit various modes of action and it would be of significant utility to increase their cytotoxicity toward cancer cells while not increasing overall systemic toxicity.

The tumor-promoting phorbol diester TPA (12-O-tetradecanoyl phorbol-3-acetate) has profound effects on a variety of cellular functions depending upon the type of cell treated, including either stimulation (Diamond, et al., *Int. J. Cancer* 13:721–730 (1974); Dridger and Blumberg *Cancer Res.* 37:3257–3265 (1977)), inhibition (Diamond, et al., *Nature* 269:247–249 (1977)); Cohen, et al., *Nature* 266:538–540 (1977)) of proliferation, or induction of differentiation (Dridger and Blumberg *Cancer Res.* 37:3257–3265 (1977); Diamond, et al., *Nature* 269:247–249 (1977)). The effects of TPA appear to be largely mediated through stimulation of protein kinase C and the subsequent phosphorylation of a variety of protein substrates (Blacksher, et al., *FASEB* 2: 2957–2969 (1988); Nishizuka, *Nature* 308:693–698 (1988)).

TPA has been reported to alter cellular sensitivity to several kinds of antineoplastic agents. In the human KB carcinoma cells, TPA treatment decreased sensitivity to etoposide and vincristine by 50%, but this effect could not be mimicked by treatment of cells with 1-oleoyl-2-acetylglycerol (OAG), calling into question a role for protein kinase C (Ferguson and Cheng, *Cancer Res.* 47:433–441 (1987)). Posada (Posada, et al., *J. Biol. Chem.*, in press (1990)) demonstrated that TPA enhanced the cytotoxic activity of doxorubicin in sarcoma 180 cells. Conversely, down regulation of protein kinase C produced by long term exposure to TPA resulted in a decreased cytotoxic effect of doxorubicin (Posada et al., *J. Biol. Chem.*, in press (1990)). Protein kinase C can phosphorylate the MDR 1 gene product, which functions as efflux pump for etoposide, vincristine, and doxorubicin. Hofmann (Hofmann, et al., *Int. J. Cancer* 42:382–388 (1988)) reported that either inhibition of protein kinase C activity with a series of compoundation such as quercetin (3,3', 4'5,7 -pentahydroxyflavone), tamoxifen, staurosporine, either lipid analog (BM4144026) (Hofmann, et al., *Lipids* 24:312–317 (1989)), or down regulation with long term exposure to TPA enhanced the sensitivity of cells to DDP.

Platinum complexes, particularly cisplatin (DDP), are drugs of major importance in cancer therapy. However, both intrinsic and acquired resistance to DDP occurs frequently. Cells selected for resistance to many antimetabolites (Kaufman, et al., *Proc. Natl. Acad. Sci. U.S.A.* 76:5669 (1979)), and to drugs participating in the multiple drug resistance phenotype (Gottesman and Pastan, *J. Biol. Chem.* 263:12163 (1988)), often exhibit very high levels of resistance. In contrast, both in vitro and in vivo selection with DDP at clinically relevant intensities usually results in cells only 2 to 4-fold resistant to this drug (Wilson, et al., *Br. J. Cancer* 56: 763 (1987)). Attempts to enhance the sensitivity to DDP have focused on strategies such as reduction of glutathione (Andrews, et al., *Chem. Biol. Interactions* 65:51 (1988)) and inhibition of DNA repair (Hamilton, et al., *Proc. A. Assoc. Cancer Res.* 28:291 (1987)).

SUMMARY OF THE INVENTION

The present invention discloses a method of sensitizing cancer cells to various cytotoxic agents and augmenting such sensitivity with various sensitizing agents. The present invention comprises administering a sensitizing agent selected from the group consisting of Epidermal Growth Factor (EGF), the tumor promoting phorbol diester TPA (12-O-tetradecanoyl phorbol-3-acetate), retinoic acid, estrogen, progesterone, triiodothyronine, androgens and analogs thereof to an individual in need of such treatment.

The term "analog" means any structurally related compound which mimics the biological activity of a sensitizing agent. Of particular interest as analogs are the steroid-like analogs of estrogen, progesterone, and the androgens.

The sensitizing agent is preferably administered in advance of or concurrently with the cytotoxic agent. In one embodiment, the sensitizing agent is administered following the administration of the cytotoxic agent. The sensitizing agent is administered in an amount which causes an increased sensitivity of the cancer cells to the cytotoxic agent and thus, enhances the efficacy of the cytotoxic agent.

In another embodiment, the sensitizing agent additionally increases the selectively of the cytotoxic drug. For instance, one skilled in the art will recognize that the modulators of cisplatin sensitivity will increase the toxicity of cisplatin by enhancing the effectiveness of cisplatin on cells which have receptors for the sensitizing agent. As is discussed herein, several types of human tumors such as malignant glioma, adrenal carcinoma, hepatoma, ovarian, lung and breast carcinoma are known to express greater numbers of EGF receptors than normal cells (Libermann et al., *Cancer Res.* 44: 753 (1984); Xu et al., *Proc. Natl. Acad. Sci. USA* 81:7308 (1984); Kamata et al., *Cancer Res.* 46:1648 (1986); Meyers et al., *J. Cell Biochem.* 38: 87 (1988); Bauknect et al., *Gynec. Oncol.* 29: 147 (1988)). Therefore, not only will there be an enhanced cytotoxic effect of drugs whose cytotoxicity is increased by EGF, but it will be selectively augmented in cells containing higher numbers of EGF receptors. The term "selectively" as used in this context means the ability of the sensitizer or modulator to increase the toxicity of the cytotoxic drug to a greater extent in abnormally proliferating cells than in normal cells.

In a preferred embodiment, the cytotoxic agent is cisplatin. However, other cytotoxic agents such as carboplatin, tetraplatin, taxol, melphalan and 5-fluorouracil may also be utilized to practice the present invention. In one specific embodiment, one skilled in the art can readily determine the effective dosage of the sensitizing agent by reference to the amount of TPA utilized in vitro which increases the sensitivity in cultured human ovarian carcinoma cells to various cytotoxic drugs. Since TPA produces this effect via protein kinase C, one will readily ascertain that other agents which act through the protein kinase C pathway will also be useful in practicing the present invention. For example, the inventors have demonstrated that this sensitizing effect occurs in the absence of a change in cellular accumulation of DDP and thus implicates a phosphoprotein as a major determinant of the activity of DDP once it has entered the cell. In addition, one of skill in the art will readily recognize that since the naturally occurring signal transduction pathway, mediated by epidermal growth factor (EGF), can both enhance sensitivity to DDP, and produce morphologic changes consistent with activation of a differentiation program in two human ovarian carcinoma cell lines, other agents which mimic this effect of EGF will also be useful in practicing this invention.

In another embodiment, the sensitizing agent is also useful to modulate the repair of DNA adducts or lesions caused by the cytotoxic agents. For instance, when a sensitizing agent such as EGF is administered after the administration of the cytotoxic agent cisplatin, the normal cellular mechanism for repairing DNA are diminished. Therefore, in cells damaged by, for instance, cisplatin the normal cellular DNA repair mechanisms are decreased or inhibited in the presence of a sensitizing of a sensitizing agent such as EGF by the inhibitory effect of the EGF on the normal cellular DNA repair mechanism.

DETAILED DESCRIPTION OF THE INVENTION

The following cell lines were used in these studies: 2008 human ovarian carcinoma (Disaia, et al., *Am. J. Obstet. Gynecol.* 114:978 (1972)), COLO 316 human ovarian carcinoma (Woods et al., *Cancer Res.* 39:4449 (1979)), a DDP resistant variant 2008/C13*, derived from the parent 2008 cell line (Andrews, et al., *Cancer Res.* 45:6250 (1985)), A549 non-small cell lung cancer (Lieber et al., *Int. J. Cancer* 17:62 (1976)), NCI-H520 squamous cell lung cancer (Brower et al., *Cancer Res.* 46: 798 (1986)), NCI-H596 adenosquamous lung cancer (Banks-Schlegel et al., *Cancer Res.* 45: 1187 (1985)), UMC 31 small cell lung cancer cells (Graziano et al., *Genes, Chromosomes and Cancer* 3: 283 (1991)), GLC4 small cell lung cancer cells (Zijlstra et al., *Cancer Res.* 47: 1780 (1987)), UMCC10b head and neck cancer cells (Krause et al., *Arch. Otolayngol.* 107: 703

(1981)), 5637 bladder cancer cells (Fogh et al., *J. Natl. Cancer Inst.* 58: 209 (1977)), MIA PaCa-2 pancreatic cancer cells (Yunis et al., *Int. J. Cancer* 19:128 (1977)), Du 145 prostate cancer (Mickey *Cancer Res.* 37: 4049 (1977)), COLO 205 colon cancer (Semple et al., *Cancer Res.* 38:1345 (1978)), KB-3-1 cervix cancer (Akiyama et al., *Somat. Cell Mol. Genet.* 11: 117 (1985)), MCF-7 breast cancer (Soule et al., *J. Natl. Cancer Inst.* 51:1409 (1973)), A431 epidermoid carcinoma of the skin (Giard et al., *J. Natl. Cancer Inst.* 51: 1417 (1973)) and T-289 melanoma cells (Taetle et al., *Cancer (Philadelphia)* 60: 1836 (1987)). The human cell line 2008 was established from a patient with a serous cystadenocarcinoma of the ovary. The 8-fold DDP resistant cell line 2008/C13* was generated by 13 monthly selections with 1 DDP, followed by chronic exposure to stepwise increasing concentrations of DDP, from 0.25 to 5 uM. A resistant subline, designated 2008/C13*5, was obtained by monthly selections with 1 µM DDP. The cells were grown on tissue culture dishes in a humidified incubator at 37° C. and 5% $CO_2$ atmosphere. Cells were grown in either of the following types of media: RPMI 1640, RPMI 1640 plus HITES buffer, DMEM low glucose, or DMEM high glucose supplemented with 5% to 10% heat inactivated fetal calf serum and 2 mM glutamine.

Colony forming assays were used to assess the effect of each drug on the sensitivity of various tumor cell lines to cytotoxic agents (Andrews, et al., *Chem.-Biol. Interact* 65:51–58 (1988)). For assays performed on plastic tissue culture dishes, five ml of suspended cells were plated on 60-mm polystyrene tissue culture dishes (Corning Glass Works, Corning, N.Y.). Cells were allowed to attach overnight, then 10 µl of stock drug solution was added to triplicate plates at each drug concentration. Control plates received diluent alone. After 1 h, the drug-containing medium was aspirated and replaced with drug free medium. Plates were incubated in humidified 5% $CO_2$ air, and after 14 days plates were fixed with methanol and stained with Giemsa. Colonies of over 60 cells were counted macroscopically.

For assays performed in soft agar, cells were trypsinized and resuspended in complete medium, aliquotted at 2 ml containing 10,000 cells per ml, and exposed to the cytotoxic drug and EGF concurrently for 1 hour. The drug containing media was removed and cells were resuspended in 5 ml of complete medium containing 0.36% low melting-temperature agarose at 37° C. The cell suspension was mixed well and then aliquotted at 1 ml per dish in triplicate onto prepared 35 mm dishes containing a basement layer of solidified 1% agarose. The cell-containing layer was allowed to solidify at 4° C. for 10 minutes, and the dishes were incubated at 37° C. in humidified 5% $CO_2$. Colonies greater than 125 um were counted after 5 days.

Figure 1A:
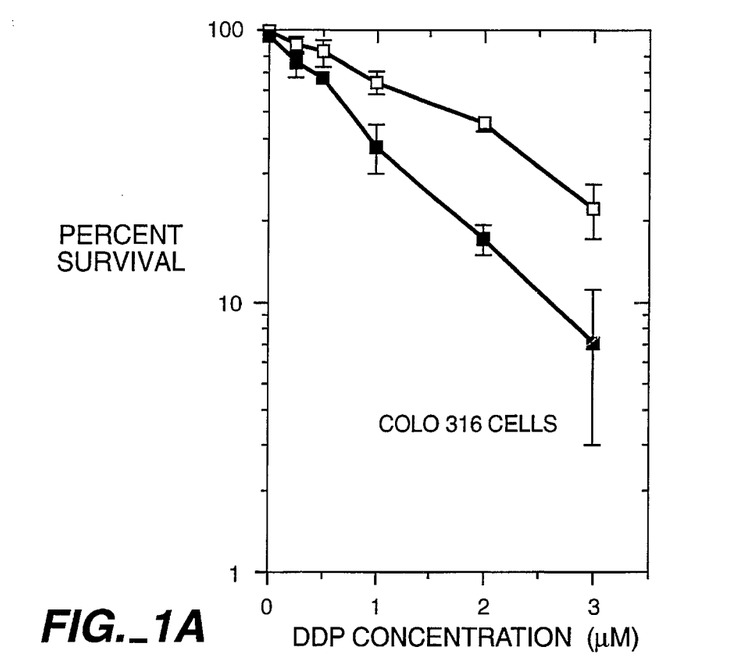
FIG. 1A demonstrates the effect of EGF on sensitivity to the cytotoxic effect of DDP in COLO 316 cells.
Figure 1B:
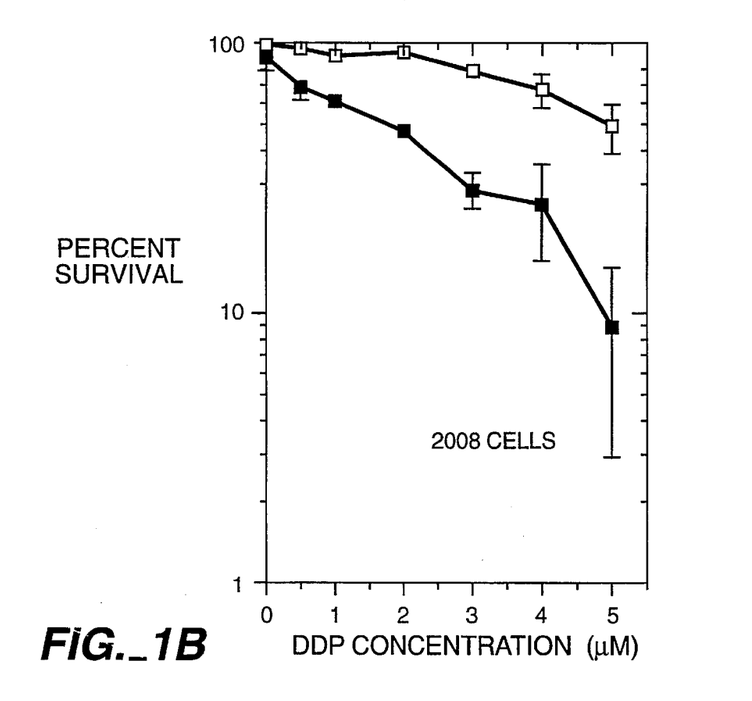
FIG. 1B demonstrates the effect of EGF on sensitivity to the cytotoxic effect of DDP in 2008 cells.
Figure 2A:
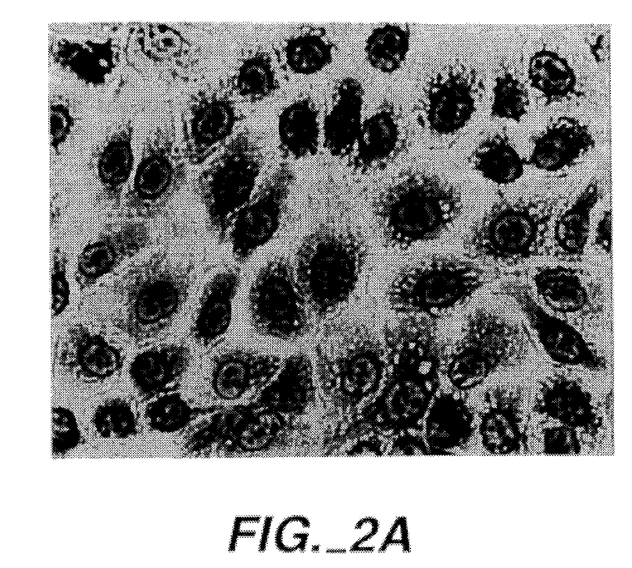
FIG. 2A demonstrates the morphology of untreated COLO 316 cells.
Figure 2B:
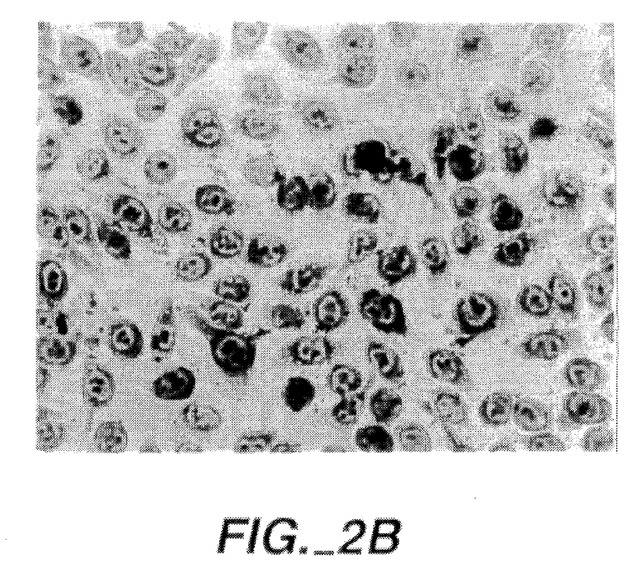
FIG. 2B demonstrates the morphology of untreated 2008 cells.
Figure 2C:
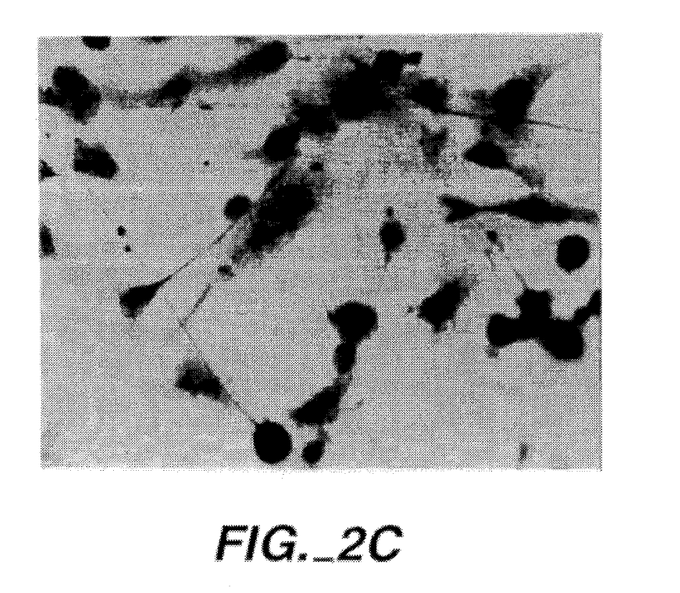
FIG. 2C demonstrates the morphological changes induced by EGF in COLO 316 cells.
Figure 2D:
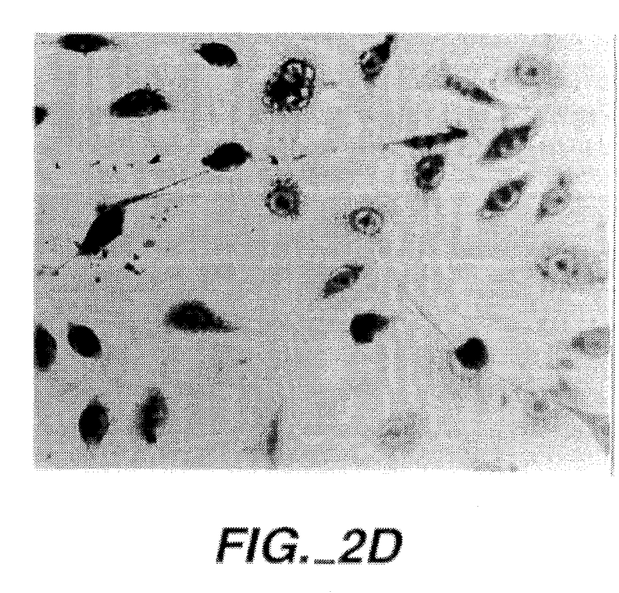
FIG. 2D demonstrates the morphological changes induced by EGF in 2008 cells.

The effect of EGF on the sensitivity of 2008 and COLO 316 cells to DDP is shown in FIG. 1. FIG. 1 demonstrates the effect of EGF on sensitivity to the cytotoxic effect of DDP. 2008 cells and COLO 316 cells were maintained in exponential growth in RPMI Medium 1640 supplemented with 5% heat-inactivated bovine calf serum, 2 mM freshly added glutamine, and 1% Fungi-bact (Irvine Scientific, Santa Ana, Calif.). Clonogenic assays were performed by seeding 300 cells per 60 mm plastic dish (Corning Glass Works, Corning, New York, N.Y.). Cells treated with EGF (murine EGF, Sigma Chemical Co, St. Louis, Mo.) were exposed to 10 nM EGF for 1 h and then to both EGF and DDP during the second h. The colonies that formed were counted after 10 days of incubation in humidified 5% $CO_2$ at 37° C. Cell clusters containing more than 50 cells were scored as colony. Open squares, DDP alone; closed squares, DDP and EGF. Data points (±SD) are the mean of 3 separate experiments each performed with triplicate cultures.

Cells were exposed to 10 nM EGF for 1 h, and then to both EGF and DDP during a second h. EGF increased the sensitivity of 2008 cells by 2.9-fold, as quantified by the ratio of the slopes of the dose-response curves, and by 3.8-fold, as quantified by the ratio of the $IC_{50}$ values. In the COLO 316 cells increase in sensitivity was 1.7-fold, as quantified by the ratio of the slopes, and 2.0-fold, as quantified by the ratio of the $IC_{50}$ values. The EGF-induced change in slope of the DDP dose response curve was significant for both the 2008 and the COLO 316 cell lines ($P>0.016$, and $P>0.031$, respectively, by two-sided t-test for the comparison with entreated cells). EGF did not alter DDP cytotoxicity to 2008/C13* cells.

The observed modulation of sensitivity to DDP by EGF was not due to an EGF-induced change in growth rate. The effect of both a 2 h exposure and continuous exposure to 10 nM EGF on growth rate was assayed using the same culture conditions under which EGF enhanced sensitivity to DDP. During the first 5 days after cell seeding, cell growth was exponential. The doubling times of the 2008, 2008/C13*, and COLO 316 cells were 27.9, 28.2, and 29.2 hs, respectively. Neither a 2 h nor a continuous exposure to 10 nM EGF had any demonstrable impact on the growth rate of these cell lines.

The effect of EGF concentration on the sensitivity of 2008 cells was concentration dependent. A 2 h exposure to EGF (1 h before and 1 h concurrent with DDP) enhanced sensitivity to DDP at EGF concentrations as low as 0.4 nM, and the effect was maximal at concentrations of about 10 nM (approximately 1.5 times the KD of the EGF receptor). As expected, a further increase in the EGF concentration up to 100 nM produced no additional change in sensitivity to DDP. The EGF-induced increase in sensitivity was not dependent on new protein synthesis. Under circumstances where DDP and EGF together reduced 2008 survival to 31±10% of control cells treated with DDP alone, pretreatment with cyclohexamide sufficient to inhibit protein synthesis by 90% produced a survival of 47±8%.

The time course of the EGF effect on the sensitivity of 2008 cells was determined by exposing cells to 10 nM EGF for 1 h, and to DDP either concurrently or with an increasing delay between the 1 h EGF pre-treatment and 1 h DDP exposure. When given concurrently with DDP, EGF significantly increased sensitivity to DDP reducing survival to 58+12% (SD) of that of control cells treated with DDP alone. Sensitivity to DDP increased even further when cells were exposed to EGF for 1 h prior to treatment with DDP with survival being reduced to 40+5% (SD) of control. The EGF mediated increase in sensitivity to DDP persisted for at least 6 hs, but had largely disappeared by 24 hs.

In addition to enhancing sensitivity to DDP, and despite the lack of effect on growth, a 2 h exposure to EGF had marked effects on the morphology of the 2008 and COLO 316 cells. FIG. 2 demonstrates the morphologic changes induced by EGF. Cells were seeded on 60 mm plastic dishes at a density of 300 cells per dish, allowed to attach overnight and exposed to 10 nM EGF for 2 hs on the following day. Colonies were inspected by light microscopy after 10 days of incubation in the absence of EGF. Untreated cells (COLO 316 cells, left upper panel; 2008 cells, right upper panel) showed a dense monolayer of ovoid cells with round nuclei and dense chromatin. The colonies formed by the COLO 316 cells appeared somewhat denser. The lower panels show cells exposed to EGF (COLO 316, left panel; 2008 cells, right panel). In both cell lines, EGF induced a marked scattering of the colonies and the formation of prominent dendritic processes.

At the macroscopic level, colonies formed by the 2008 and COLO 316 cells 10 days after a 2 h exposure to 10 nM EGF were much larger and stained less intensely with Giemsa. At the microscopic level, colonies formed from untreated cells consisted of tightly packed cells, whereas colonies arising after EGF treatment consisted of widely scattered cells of which 10 to 20% had formed prominent dendritic processes. It was of particular interest that 2008/C13* cells, in which EGF failed to alter DDP responsiveness, showed no morphologic response to a 2 h EGF exposure.

The $K_D$ of the EGF receptor and the receptor number per cell were determined by Scatchard analysis (Scatchard, *Ann. N.Y. Acad. Sci.* 51:660 (1949)) in the DDP sensitive 2008 and COLO 316 cells, and the DDP resistant 2008/C13* subline. The data is summarized in Table 1.

$^{125}$I EGF binding assays were performed with some modifications as described by Kawamoto (Kawamato et al., *Proc. Natl. Acad. Sci. USA* 80:1337 (1983)). 3-($^{125}$I I iodotyrosyl EGF (human recombinant), specific activity 9000 Ci/mmol, was purchased from Amersham Corporation (Arlington Heights, Ill.). Subconfluent 2008, 2008/C13*, and COLO 316 cells grown in 150×25 mm plates were fixed with 0.2% paraformaldehyde for 10 minutes at room temperature to prevent receptor internalization during incubation with EGF (Willingham et al., *J. Biol. Chem.* 82:614 (1979)). Cells were scraped off with a rubber policeman and washed 3 times with PBS (phosphate buffered saline containing 0.2% bovine serum albumin (PBS/albumin) and resuspended in the same buffer at a cell density of 5×10$^6$ per ml. For binding assays, 200 µl of cell suspension (approximately 1×10$^6$ cells) were incubated with 1 uCi dissolved in 200 µl PBS/albumin. After a 2 h incubation, cells were quantitatively collected on low protein binding hydrophilic Durapore membranes (pore size 0.22 µm, purchased from Millipore Corporation, Bedford, Mass.) by suction. To prevent nonspecific binding of EGF, the filters were prewet with PBS/albumin. After cell collection, the filters were washed 5 times with PBS/albumin. The filters were dried and radioactivity was measured in a gamma counter. Calculation of receptor number and $K_D$ was performed as described by Scatchard. Mean and standard deviation of 3 different experiments are shown.

TABLE 1

| Cell Line | Scatchard Analysis of EGF Binding | | |
| --- | --- | --- | --- |
| | Fold Increase in Resistance to DDP | Number of EGF Receptors Per Cell (× 10$^4$) | Dissociation Constant ($K_D$, nm) |
| 2008 | 1 | 16.5 ± 0.7 | 2.4 ± 1.3 |
| 2008/C13 | 8 | 5.8 ± 0.9[1] | 4.0 ± 0.3 |
| COLO 316 | 1 | 4.3 ± 0.4 | 4.0 ± 1.4 |

[1] p > 0.0007 by two-sided t-test for the comparison with 2008 cells.

The Scatchard plots were monophasic in all cell lines examined, suggesting the presence of a single class of EGF receptors, with the same $K_D$. The $K_D$ and EGF receptor number per cell for 2008 and 2008/C13* cells were of the same order of magnitude. Thus, neither the absolute receptor number nor the $K_D$ predicted the ability of EGF to modulate DDP responsiveness, whereas resistance to DDP rendered the cells refractory to EGF enhancement of DDP sensitivity and EGF induced changes in cell morphology.

The functionality of the EGF receptors was assayed in 2008 cells and 2008/C13* cells by demonstrating down-regulation of the receptor number upon binding to EGF. The receptor number was determined by staining with mAB455, specific for the human EGF receptor, which does not competitively inhibit the binding of EGF to it's receptor (Sato, et al., *Mol. Biol. Med.* 1:511 (1983); Kawamoto, et al., *Anal. Biochem.* 130:445 (1983)). A 1 h incubation of 2008 and 2008/C13* cells with 100 pM EGF at 37° C. caused down regulation of 60–70% of the EGF receptors on both types of cells as compared with control cells treated with 100 nM EGF for 1 h on ice (a condition known to prevent receptor down-regulation). Using EGF receptor mutants lacking intrinsic protein-tyrosine kinase activity, it has been convincingly shown that tyrosine-kinase activity is essential for signal transduction and for receptor down-regulation upon binding to EGF (Honegger et al., *Cell* 51:199 (1987); Honegger et al., *Mol. Cell Biol.* 7 (12):4568, (1987)). Therefore, it can be concluded that both the 2008 and 2008/C13* cells have functional EGF receptors.

Figure 3:
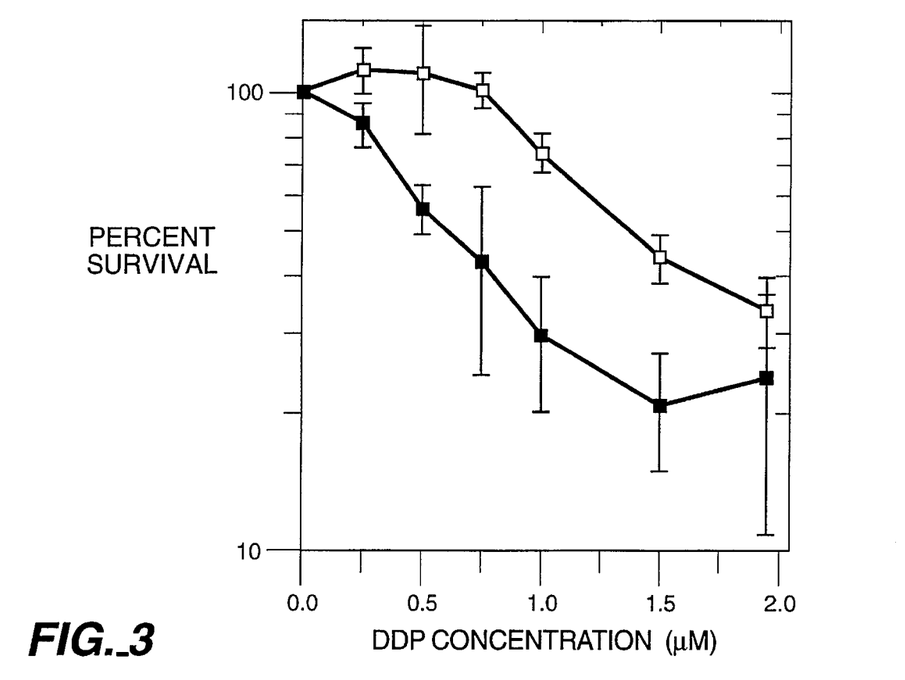
FIG. 3 demonstrates the effect of EGF receptor number on cell response to DDP.

To demonstrate that the modulating effect of EGF on sensitivity to DDP was transduced by the EGF receptor, the effect of EGF on the DDP sensitivity of mouse fibroblast C127 cells stably transfected with a plasmid construct containing the human EGF receptor gene under the control of the transferrin receptor 3' inducible regulator (McClelland, et al., *Cell* 39:267 (1984)) was examined. Expression of the transferrin receptor gene is normally under the control of the transferrin 3' inducible regulator, and is regulated by iron (Owen and Kuhn, *EMBO J.* 6:1287 (1987)). Incubation with the iron chelator desferrioxamine induces expression of the transferrin receptor gene (Bridges and Cudkowicz, *J. Biol. Chem.* 259:12970 (1984)). Expression of the human EGF receptor in transfected cells was visualized by staining with the monoclonal antibody 528 specific for the human EGF receptor (Sato, et al., *Mol. Biol. Med.* 1: 511 (1983); Kawamoto, et al., *Anal. Biochem.* 130:445 (1983)). Desferrioxamine 10 nM increased the number of human EGF receptors by approximately 2-fold. Since C127 cells do not form uniform colonies, the sensitivity of control and desferrioxamine-induced cells to DDP was compared by using a growth rate assay in which the cell number was quantified by tetrazolium dye reduction (Scudiero et al., *Cancer Res.* 48:4827 (1988)). Desferrioxamine at a concentration of 10 µM was non-toxic to transfected C127 mouse fibroblasts even after prolonged incubation for 2 weeks, and did not modulate the sensitivity of transfected C127 cells in the absence of EGF. FIG. 3 demonstrates the effect of EGF receptor number on cell response to DDP. Closed squares, transfected C127 mouse fibroblasts pretreated with desferrioxamine; open squares, untreated cells. C127 mouse fibroblasts were transfected with the human EGF receptor gene under control of the transferrin 3' inducible regulator. One aliquot of cells was incubated in 10 µM desferrioxamine for 60 hs which induced EGF receptor expression approximately 2-fold, while another was cultured under identical conditions in the absence of desferrioxamine. Using the tetrazolium assay, the effect of DDP on growth rate was determined by seeding 1500 cells in 180 µl of Dulbecco's Modified Eagle Medium (DME) containing 4.5 gm per liter glucose, 10% heat inactivated fetal calf serum, 25 ug/ml human transferrin (holo-form), and 10 pM EGF. DDP at different concentrations was added in 20 µl of saline to triplicate culture wells, and cultures were incubated for 6 days in humidified 5% CO2 in air at 37° C. MTT 3-(4,5-dimethylthiazol-2-yl)-2,5-diphenyl tetrazolium bromide (Sigma, St. Louis, Mo.) was prepared at 1 mg/ml in DME media and on day 7, 50 μl are added to the microculture wells. After a 4 h incubation at 37° C., all the media was removed from each well, and 150 μl of 100% DMSO (dimethyl sulfoxide) was added to solubilize the MTT-formazan product. After thorough mixing, absorbance at 540 nm was measured with a Molecular Devices Vmax Kinetic microplate reader.

FIG. 3 shows that, in the presence of 10 nM EGF, the desferrioxamine treated, transfected C127 cells were approximately 2-fold more sensitive to the cytotoxicity of DDP than control cells. Thus, within a cell line sensitivity to DDP can be regulated by both EGF and EGF receptor number.

These results indicate that sensitivity to DDP can be regulated by both EGF concentration and EFG receptor number, and this provides strong evidence that the effect was, in fact, mediated via the EGF receptor. The rapid onset of the EGF effect and the fact that it was not blocked by cyclohexamide suggest that the enhanced sensitivity is a direct result of the protein phosphorylation cascade initiated by the EGF receptor. The results also indicate that the ability of EGF to enhance sensitivity is linked with its ability to induce a change in cell morphology. EGF produced both effects in the DDP-sensitive 2008 cells, but neither effect in the DDP-resistant 2008/C13* cells. Thus, the DDP-resistant cells have one or more defects in the EGF signal transduction pathway. The ability of EGF to induce receptor down-regulation indicates that the initial steps in the signal transduction pathway, i.e., binding of EGF to it's receptor and receptor autophosphorylation, are intact in both the DDP sensitive and resistant cells. One of skill in the art will readily see that the foregoing assays may be utilized to assess the usefulness of other agents related to EGF or its pathway, to practice the present invention.

To further expand the results demonstrating that treatment with EGF results in increased cisplatin toxicity, EGF was also analyzed for it's ability to sensitize 2008 cells to several other clinically important chemotherapeutic agents. The colony forming assays described above were employed to study the effect of EGF on the sensitivity of 2008 human ovarian carcinoma cancer cells to carboplatin, tetraplatin, 5-fluorouracil, taxol, melphalan, doxorubicin and 4-hydroperoxycyclophosphamide.

The effect of EGF on the sensitivity of 2008 cells to these additional chemotherapeutic agents is shown in Table 2. Table 2 demonstrates that in 2008 cells, EGF induces a significant increase in sensitivity to not onlylcisplatin, but also to carboplatin, tetraplatin, taxol, and 5-fluorouracil. EGF enhanced the cytotoxicity of these agents from 1.4 to 1.8 fold (statistically significant at p<0.05). EGF also increased the sensitivity of 2008 cells to melphalan, however, the effect did not reach the level of statistical significance. EGF had no significant effect on the sensitivity of 2008 cells to doxorubicin or 4-hydroperoxycyclophosphamide.

TABLE 2

Effect of EGF on the sensitivity of 2008 ovarian carcinoma cells to different chemotherapeutic agents

| Cell line | Cytotoxic agent | $IC_{50}$ in absence and presence of EGF[a] | Dose modifying factor[b] | p Value[c] |
|---|---|---|---|---|
| 2008 | cisplatin | 2.8/0.9 μM | 3.1 ± 0.9 | 0.027 |
| 2008 | carboplatin | 120/67 μM | 1.8 ± 0.4 | 0.022 |

TABLE 2-continued

Effect of EGF on the sensitivity of 2008 ovarian carcinoma cells to different chemotherapeutic agents

| Cell line | Cytotoxic agent | $IC_{50}$ in absence and presence of EGF[a] | Dose modifying factor[b] | p Value[c] |
|---|---|---|---|---|
| 2008 | tetraplatin | 10/6 μM | 1.6 ± 0.1 | 0.033 |
| 2008 | 5-fluorouracil | 20/11 μM | 1.8 ± 0.3 | 0.022 |
| 2008 | taxol | 10/7 nM | 1.4 ± 0.1 | 0.003 |
| 2008 | melphalan | 12/9 μM | 1.4 ± 0.4 | 0.084 |
| 2008 | doxorubicin | 1.5/1.4 μM | 1.1 ± 0.2 | 0.636 |
| 2008 | 4-OH cyclophosphamide | 40/44 μM | 0.9 ± 0.5 | 0.634 |

[a]Dose response curves were determined by colony forming assay. Cells were exposed to EGF and the cytotoxic agent concurrently for 1 h.
[b]The dose modifying factor represents the ratio of the $IC_{50}$ values in control and EGF-treated cells. Mean ± SD of at least 3 different experiments are shown.
[c]Comparison of the $IC_{50}$ values of the cytotoxic agent in the absence versus presence of EGF by 2-sided t test.

EGF was also studied for its ability to enhance the cytotoxicity of cisplatin in a number of cell lines representative of various clinically important types of human malignancies derived from various tissues of origin. To measure the effect of EGF on cisplatin toxicity in these various cell lines, cells were exposed to EGF and cisplatin concurrently for 1 hour. The concentration of EGF was fixed at 10 nM, and the concentration of cisplatin was varied to generate a survival curve spanning 2 logs of tumor cell kill.

Table 3 summarizes the effect of EGF on the cisplatin sensitivity of all the cell lines tested. The results in Table 3 demonstrate that EGF significantly enhances cisplatin toxicity in a number of cell lines derived from various tissues of origin including cancers of the head and neck, ovary, cervix, colon, prostate, pancreas as well as non-small cell cancer of the lung (type II alveolar epithelial cells). In these cell lines, EGF enhanced cisplatin toxicity from 1.4 to 3.8 fold. EGF failed to increase the cytotoxicity of cisplatin in cell lines representative of melanoma and carcinoma of the breast as well as small cell lung cancer.

TABLE 3

Effect of EGF on cisplatin sensitivity in different cell lines

| Type of cell line | Name of cell line | $IC_{50}$ in absence and presence of EGF[a] | Dose modifying factor[b] |
|---|---|---|---|
| Head and neck cancer | UMSCC 10b | 6.76/1.76 | 3.8 |
| Non-small cell lung cancer | A549 | 14.47 | 2.0 |
| Ovarian carcinoma | 2008 | 2.45/0.91 | 2.7 |
| Cervix cancer | KB-3-1 | 9.71/4.79 | 2.0 |
| Colon cancer | COLO 205 | 27.60/16.54 | 1.7 |
| Prostate cancer | Du 145 | 8.52/5.52 | 1.5 |
| Pancreatic cancer | MIA PaCa-2 | 7.65/5.53 | 1.4 |
| Breast cancer | MCF-7 | 3.82/3.80 | 1.0 |
| Small cell lung cancer | UMC 31 | 5.40/6.86 | 0.8 |
| Small cell lung cancer | GLC 4 | 12.2/18.24 | 0.7 |
| Malignant melanoma | T-289 | 2.02/2.49 | 0.8 |

[a]Dose response curves were determined by colony forming assay. Cells were exposed to EGF and the cytotoxic agent concurrently for 1 h.
[b]The dose modifying factor represents the ratio of the $IC_{50}$ values in control and EGF-treated cells.

Because EGF enhances the toxicity of various chemotherapeutic agents in numerous different cell lines, it follows that the biochemical and molecular mechanisms that mediate this effect are common to multiple cell types and that chemosensitization by EGF is not dependant on a specific biochemical pathway unique to one or another type of cancer cell. These results also indicate that the underlying mechanism of EGF-induced sensitization is not specific to one particular chemotherapeutic agent. Therefore, these results suggest that EGF acts to alter one or more components of the cellular damage response that are common between both various types of cancer cells and classes of drugs that are fundamental to cell survival.

To measure the potential of EGF to increase the sensitivity of cancer cells to cisplatin in vivo, the effect of EGF on cisplatin toxicity against 2008 tumor xenografts in athymic mice was analyzed. For these studies, 3 to 4 week old female athymic mice (nu/nu) from BALB/c origin were used which were supplied by Harlan Sprague Dawley, Inc. (Indianapolis, Ind.). The mice were kept in a laminar flow hood at 28° C. and fed standard mouse diet and water ad libitum.

Tumor xenografts were established from 2008 cells by harvesting confluent cell cultures by trypsinization and resuspending the cells in RPMI 1640 medium at $2.5 \times 10^7$ cells per ml. From this suspension, 0.2 ml aliquots containing $5 \times 10^6$ cells were injected s.c. on each shoulder of the athymic mice. In each mouse, two tumors were followed and tumor volumes were determined using the formula (length× width$^2$)/2 (Giavazzi et al., *Cancer Res.* 46:1928 (1986) and Tomayko & Reynolds *Cancer Chemother. Pharmacol.* 24:148 (1989)).

Mice were then divided into four treatment groups, (1) control mice received no treatment (5 mice, 10 xenografts), (2) ten mice (20 xenografts) were treated with 1 mg/kg EGF administered s.c. between the shoulders, (3) ten mice (20 xenografts) were treated with 15 mg/kg cisplatin i.p. and (4) ten mice (20 xenografts) received 15 mg/kg cisplatin i.p. followed immediately by 1 mg/kg EGF s.c.. In all groups, treatment was administered 24 hours after the inoculation with tumor cells.

Tumor growth of each tumor in each animal was expressed as plot of ln(tumor volume) as a function of time. The regression line of the ln(tumor volume) versus time plot was calculated by using the method of least squares. The intercept and slope were obtained and used to calculate the time each tumor required to reach an arbitrarily defined volume of 1 ml. This volume was chosen because most tumors in all treatment groups reached this endpoint. For comparisons between two groups the unpaired Student's T-test was used. One way analysis of variance (ANOVA) was performed to compare data between 3 or more treatment groups. The F-test was used to test the null hypothesis that there was no difference of a given parameter between the treatment groups. When the F-test indicated the presence of significant differences between treatment groups, the Fisher test was applied to compare any two groups. The results of these experiments are shown in FIG. 4.

Figure 4:
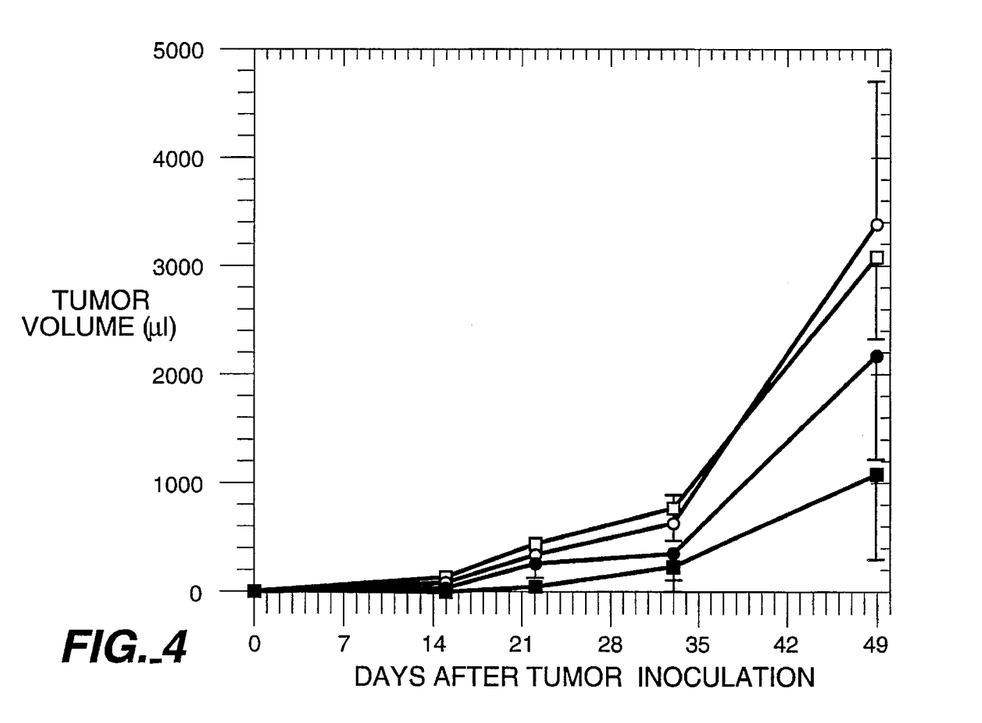
FIG. 4 demonstrates the effect of EGF on the sensitivity of 2008 tumor cell xenografts in athymic mice. Open circles (○) represent control mice which received no treatment; open squares (□) represent mice treated with 1 mg/kg EGF s.c. only; closed circles (●) represent mice treated with 15 mg/kg cisplatin j.p. only; closed squares (■) represent mice treated with 15 mg/kg cisplatin i.p. and 1 mg/kg EGF s.c.

The results in FIG. 4 demonstrate that treatment with EGF alone had no effect on the final tumor volume whereas the final volume of cisplatin treated tumors was significantly reduced relative to control tumors (P<0.01 by Fisher test). The addition of EGF significantly enhanced cisplatin-induced tumor cell kill as reflected by a further decrease in the final volume of tumors following treatment with EGF plus cisplatin relative to tumors treated with cisplatin alone (P<0.01 by Fisher test).

The time required for tumors to reach a final volume of 1 ml was calculated from the slope and intercept of the linear regression formula derived from the ln(tumor volume) versus time plot. While treatment with EGF alone had no effect on the time required for tumors to reach a volume of 1 ml, cisplatin-treated tumors required 6 days more to reach a volume of 1 ml (P<0.0001 by Fisher test for the comparison with control tumors). Treatment with EGF plus cisplatin further prolonged the time required for tumors to reach a volume of 1 ml (P<0.001 by Fisher test for the comparison with cisplatin alone).

To analyze the effect of EGF on systemic cisplatin toxicity, a first set of athymic mice was randomly divided into four different treatment groups as described above. The systemic toxicity in each treatment group was assessed by following survival and weight loss after treatment. The product limit method of Kaplan and Meier was used to determine the survival of mice in the various treatment groups (Kaplan & Meier *J. Am. Stat. Assoc.* 53:457 (1958)), and the log rank test was used for comparison of survival rates between the different treatment groups (Mantel *Cancer Chemother Rep.* 50: 163 (1966)).

Survival of mice in each treatment group was followed for 22 days following treatment. All mice treated with 1 mg/kg EGF s.c. survived. While 3 of 10 mice treated with 15 mg/kg cisplatin i.p. died, only 2 of 10 died following treatment with 15 mg/kg cisplatin i.p. plus 1 mg/kg EGF s.c. All fatalities occurred between days 6 and 9 following treatment. The survival rates of mice treated with cisplatin alone versus mice treated with cisplatin plus EGF was not statistically significant (p<0.1 by the log rank test).

Weight loss following treatment was also used as an indicator of systemic toxicity. Control mice and mice treated only with EGF exhibited a steady increase in body weight (0.16±0.09 and 0.18±0.05 gm per day, respectively) (p=0.68 by 2-sided unpaired t-test for comparison with control animals). Treatment with 15 mg/kg cisplatin i.p. resulted in substantial and rapid loss in body weight with the nadir occurring at day 7. EGF had no significant impact on the body weight loss nadir following treatment with cisplatin (p=0.94 by the 2-sided unpaired t-test for the comparison of treatment with cisplatin alone versus treatment with cisplatin plus EGF). Following day 7, mice treated either with cisplatin alone or cisplatin plus EGF regained weight at a rapid rate (0.57±0.07 and 0.59±0.14 gm per day, respectively) (p=0.83 by the 2-sided unpaired t-test). These results indicate that EGF has no significant effect on overall systemic cisplatin toxicity.

To assess the effect of EGF on cisplatin toxicity to kidney and bone marrow tissues, again mice were randomly divided into the four treatment groups described above. For nephrotoxicity studies, 72 h after treatment, mice were anesthetized and 1.5 ml of blood was sampled by cardiac puncture. Plasma creatinine and blood urea nitrogen (BUN) levels were used to measure toxicity and were determined by an enzymatic method previously described (Kulpman et al., *J. Clin. Chem. Clin. Biochem.* 28(11): 835 (1990)).

ANOVA analyses indicated that there were no significant differences in serum creatinine or BUN levels between the four treatment groups (p=0.1, and p=0.3 for creatinine and BUN, respectively, by 2-sided F-test). Neither treatment with EGF alone, cisplatin alone, or EGF plus cisplatin resulted in statistically significant increases in serum creatinine or BUN.

For analysis of bone marrow toxicity, mice from each treatment group were sacrificed 72 hs. after treatment. Blood counts and red cell indices were determined on a Serono-Baker Series 900 cell counter (Serono-Baker Diagnostics, Allentown, Pa.). The white blood cell differential was counted on blood smears stained with Giemsa.

ANOVA analyses indicated that neither treatment with cisplatin alone or treatment with cisplatin plus EGF resulted in significant alterations in white blood cell counts, absolute neutrophil counts, or hemoglobin levels (p=0.65, 0.23, and 0.79, respectively, by 2-sided F-test). Hence, these data provide additional support that, while EGF enhances cisplatin toxicity in cancer cells, it does so without altering the toxicity of cisplatin either systemically or to non-malignant target tissues such as kidney or bone marrow.

EGF produces a large number of changes in the cellular physiology of responsive cells, and at this time it is not apparent which of these contribute to the enhanced drug sensitivity. It is clear, however, that an EGF-mediated change in cell cycle phase distribution and growth rate is not required. The onset of the effect is rapid, and the time course of enhancement parallels the effect of EGF on the induction of c-myc in several other cell systems (Bravo, et al., *EMBO J.* 4:1193 (1985); (Fernandez-Pol, et al., *Biochem. Biophys. Res. Commun.* 144:1197 (1987). Recently, exposure of CaSki human squamous carcinoma cells to EGF has been shown to enhance radiosensitivity (Kwock and Sutherland, *J. Natl. Cancer Inst.* 81:1020 (1989)). It is not known whether there is a single element of the EGF signal transduction pathway capable of regulating both radiosensitivity and sensitivity to DDP, or whether different elements of the EGF signal transduction pathway are independently mediating these two effects.

The observation that EGF can modulate sensitivity to various chemotherapeutic agents in various tumor cell lines, and can commit two human ovarian carcinoma cell lines to a longlasting change in morphology consistent with activation of a differential program are important for two reasons. First, although the degree of EGF enhancement of drug sensitivity is in the range of 1.4 to 4-fold, this represents a highly clinically significant effect since most patients with acquired DDP resistance have relatively low levels of resistance. Several types of human tumors such as malignant glioma, adrenal carcinoma, hepatoma, ovarian, lung and breast carcinoma are known to express unusually large numbers of EGF receptors in vivo (Libermann et al., *Cancer Res.* 44:753 (1984); Xu et al., *Proc. Natl. Acad. Sci. USA* 81:7308 (1984); Kamata et al., *Cancer Res.* 46:1648 (1986); Meyers et al., *J. Cell Biochem.* 38:87 (1988); Bauknecht et al., *Gynec. Oncol.* 29:147 ((1988))). Thus, in practicing the present invention, EGF, as well as other sensitizing agents, can be used to selectively enhance the sensitivity of these tumors to various chemotherapeutic agents without increasing the toxicity of these to normal tissues at the same time.

The number of EGF receptors can be increased by a variety of agents available for clinical use such as retinoic acid (Thompson and Rosner, *J. Biol. Chem.* 264:3230 (1989)), estrogen (Mukku and Stancel, *J. Biol. Chem.* 260:9820 (1985)), progesterone (Murphy, et al., *Biochem. Biophys. Res. Commun.* 150:192 (1987)), tri-iodothyronine (Fernandez-Pol, *J. Biol. Chem.* 264:4151 (1989)), and androgens (Mulderet et al., *J. Steroid Biochem.* 32:151 (1989)). Thus, the present invention teaches the principle of enhancing in vivo tumor responsiveness to various chemotherapeutic drugs using one or more of these sensitizing agents. Secondly, in practicing the present invention, one may use EGF to stimulate differentiation of ovarian carcinomas, thus potentially reducing the degree of malignancy.

Other sensitizing agents are also effective in enhancing the cytotoxicity of DDP. The following Examples illustrate the effectiveness of TPA in enhancing the sensitivity of cancer cells to DDP.

EXAMPLE 1

Effect of TPA on DDP Sensitivity

Figure 5A:
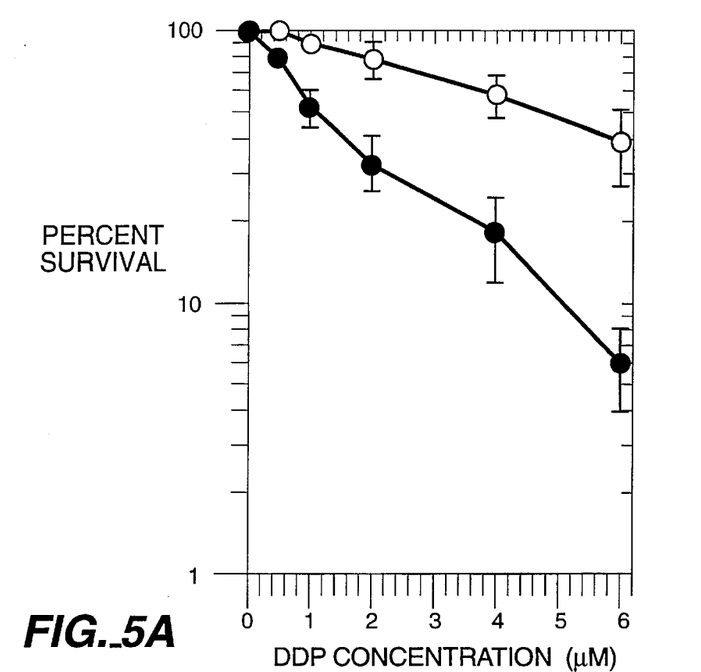
FIG. 5A demonstrates the sensitivity of 2008 cells to DDP in the presence (●) and absence (○) of $10^7$M TPA wherein cells were exposed to DDP and TPA concurrently for 1 hour.
Figure 5B:
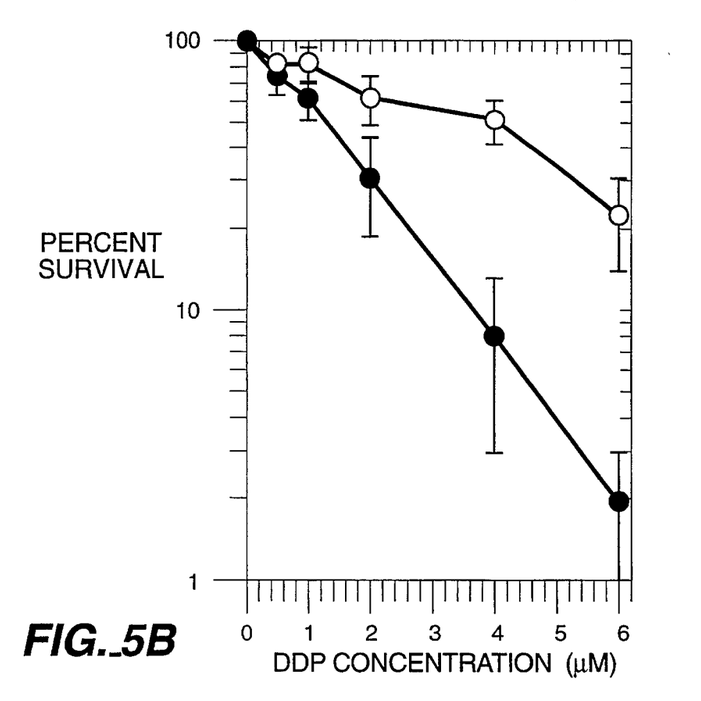
FIG. 5B demonstrates the sensitivity of 2008 cells to DDP in the presence (●) and absence (○) of $10^7$M TPA wherein cells were exposed to TPA for 24 hours followed by exposure to DDP for 1 hour.
Figure 5C:
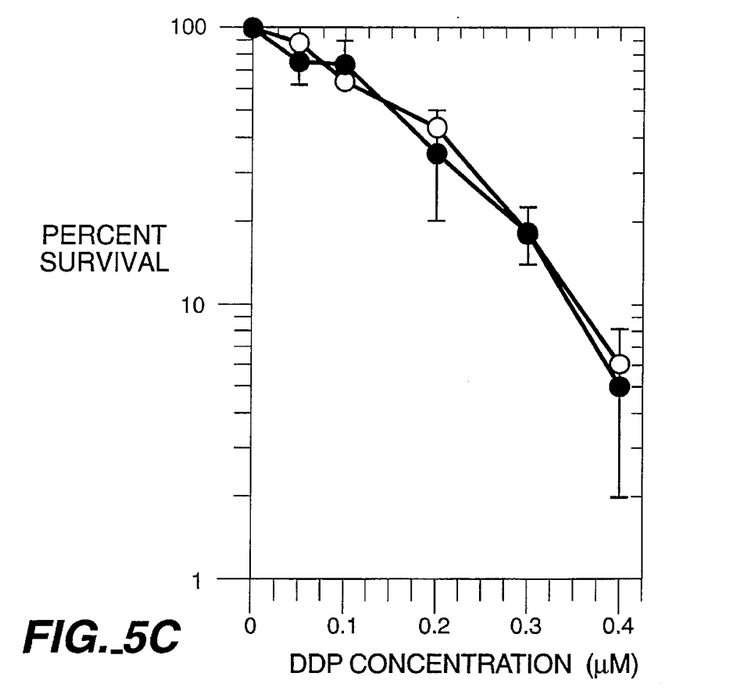
FIG. 5C demonstrates the sensitivity of 2008 cells to DDP in the presence (○) and absence (○) of $10^7$M TPA wherein cells were exposed concurrently to DDP and TPA for ten days.

One hour exposure to TPA or phorbol was performed by adding drugs at the concentration of $10^{-7}$ nM to each plate concomitantly with DDP. Stock solutions consisted of $10^{-3}$M TPA or phorbol in acetone. In assays involving continuous exposure to DDP with or without TPA, drugs were left in these cultures for the full period of colony formation. FIG. 5 demonstrates the sensitivity of 2008 cells to DDP in the presence (●) or absence (○) of $10^7$M TPA. Cells were treated as follows: Left, 1-h drug exposure to DDP concurrently with TPA; Middle, 24-h TPA pretreatment followed by 1-h exposure to DDP; Right, 10 days continuous exposure to DDP with TPA. Drug cytotoxicity was determined by colonogenic assay. Cultures not containing TPA received an appropriate dilution of acetone as a vehicle control. Points, mean values of three experiments performed with triplicate cultures; bars, S.D.

As demonstrated on FIG. 5, when 2008 cells were exposed concurrently for 1 h to 0.1 HM TPA and DDP, TPA increased DDP sensitivity. The $IC_{50}$ in the absence of TPA was 3.07±0.6 μM (S.D.), whereas in the presence of TPA it was 1.2 ±0.4 μM (S.D.). Thus, TPA produced a 2.5 fold increase in sensitivity. When cells were treated with a 24-h exposure to 0.1 μM TPA followed by a 1-h exposure to DDP, a similar degree of sensitization was observed. However, when cells were treated with continuous exposure to both the TPA and DDP for the full period of colony formation, no change in DDP sensitivity was evident. TPA at concentrations even up to 1 HM did not cause any toxicity by itself; thus, the interaction between TPA and DDP is truly synergistic as defined by median effect analysis (Chou, and Talalay, *Adv. Enzyme Requl.* 22:27–54 (1984)).

EXAMPLE 2

Time Course of Sensitization

Figure 6:
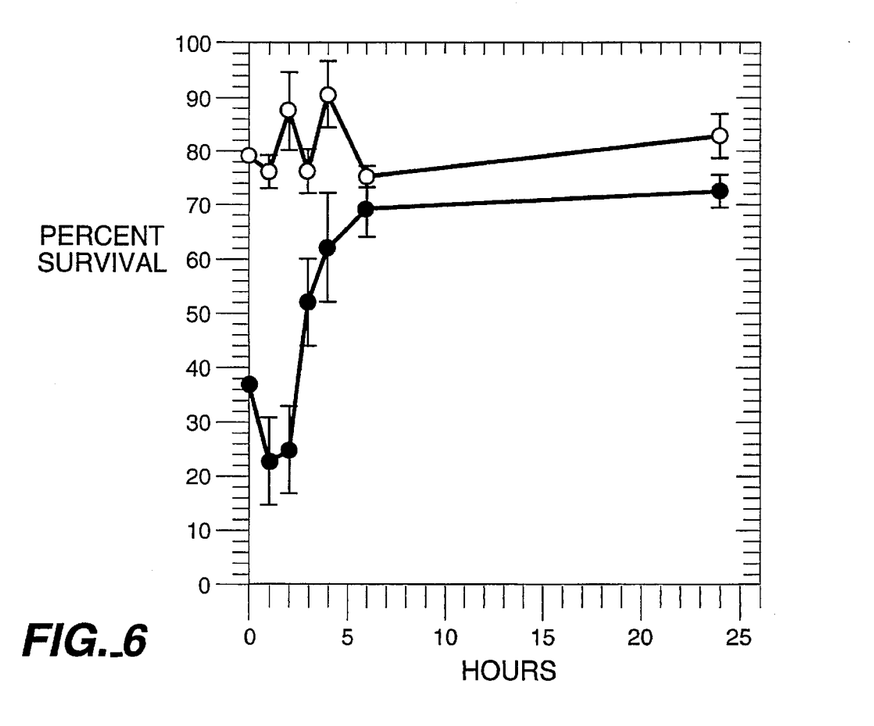
FIG. 6 demonstrates the time-course of change in DDP sensitivity in the presence (●) or absence (○) of $10^7$M TPA for 1 h.

Ovarian carcinoma 2008 cells were exposed to 0N1 μM TPA and 2 μM DDP either concurrently or with increasing time intervals between the start of 1-h TPA and DDP exposures. FIG. 6 demonstrates the time-course of change in DDP sensitivity in the presence (●) or absence (○) of $10^{-7}$M TPA for 1 h. After the appropriate drug-free incubation period, cells were treated with 2 HM DDP concurrently for 1 h. Drug cytotoxicity was determined by colonogenic assay on plastic dishes. Points, mean values of 3 experiments performed with triplicate cultures; bars, SD. FIG. 6 shows that 2 μM DDP reduced colony survival to approximately 80% in the absence of TPA. TPA sensitization was maximal between 1 and 2 h after the start of TPA exposure, but had largely disappeared by 7 h. This time course is consistent with that for activation and inactivation of protein kinase C in other cell systems (Ferguson and Cheng, *Cancer Res.* 47:433–441 (1987)).

EXAMPLE 3

DDP Accumulation

Figure 7A:
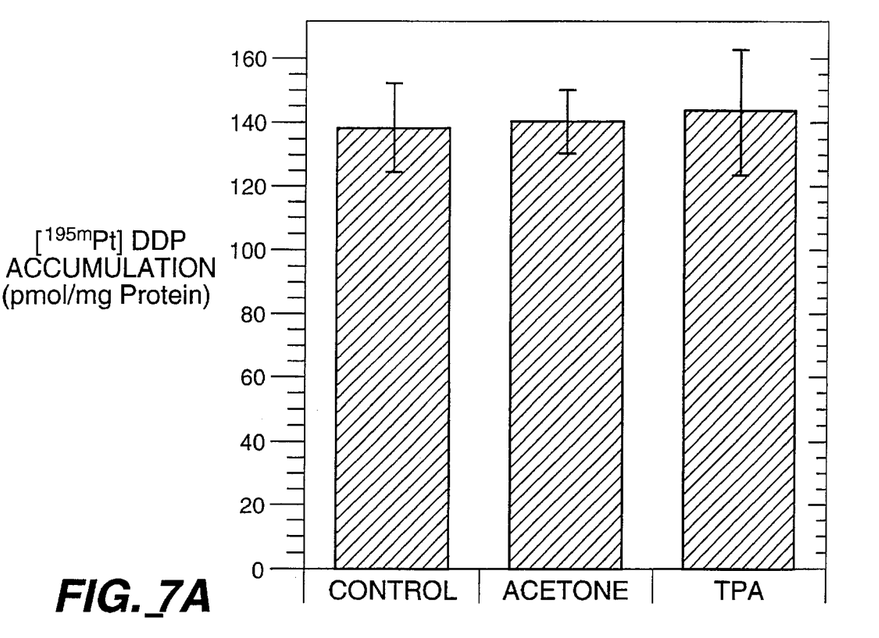
FIG. 7A demonstrates the accumulation into 2008 cells of [$^{195m}$Pt]DDP alone or in the presence of either acetone or TPA wherein cells were treated concurrently with [$^{195m}$Pt]DDP and TPA for 60 min.
Figure 7B:
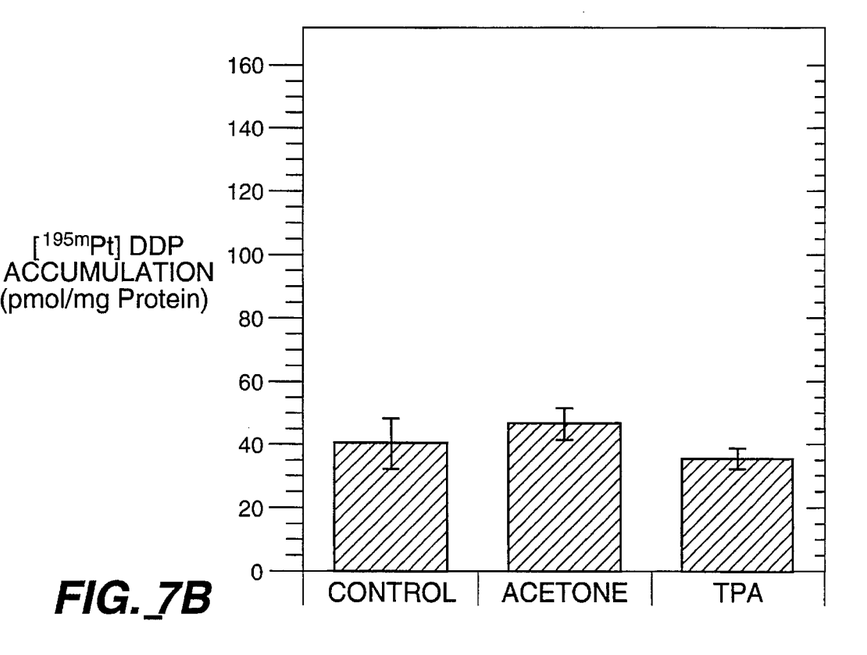
FIG. 7B demonstrates the accumulation into 2008 cells of [$^{195m}$Pt]DDP alone or in the presence of either acetone or TPA wherein cells were pre-incubated for 24 hours with TPA.

FIG. 7 demonstrates the accumulation of [$^{195m}$Pt]DDP alone or in the presence of either acetone or TPA. Cell-associated $^{195m}$Pt was determined by as a measure of DDP accumulation. For DDP accumulation studies, subconfluent monolayers were treated with 37° C. RPMI 1640 medium containing 20 μM [$^{195m}$Pt]-DDD. The dishes were immediately returned to the incubator. After 1 h incubation, the medium was aspirated, the cells were washed rapidly with 4° C. PBS 4 times. Two ml of 1N NaOH was added and the cells allowed to digest overnight. A forty μl aliquot was used for determination of protein content by the method of Bradford (Bradford, *Anal. Biochem.* 72:248–254 (1976)), and the remaining 1.6 ml was counted in glass tubes on a Trak 1191 gamma counter (Tracer Analytic, ElK Grove Village, Ill.). Columns represent the mean values of 3 experiments performed with duplicate cultures. The bars represent the standard deviation.

EXAMPLE 4

Effect of TPA on Cellular Accumulation of DDP

Cultured 2008 cells were treated concurrently with [$^{195m}$Pt]DDP and TPA for 60 min. A vehicle control consisting of an appropriate dilution of acetone was run concurrently. Panel A in FIG. 7 shows that neither the acetone nor the TPA produced any effect on cellular accumulation of [$^{195m}$Pt]DDP. Cells treated with medium alone contained 140±13 pmol/mg of protein, whereas those treated with the acetone control contained 141±7 pmol/mg of protein, and those treated with TPA contained 143±21 pmol/mg of protein. Similar experiments were conducted using either a 10-min TPA preincubation followed by a 1-h concurrent TPA and [$^{195m}$Pt]DDP exposure, or a 24-h preincubation with TPA, and none of them showed any effect on DDP accumulation. Thus, TPA altered sensitivity by a mechanism which does not involve an increased amount of drug entering the cell.

EXAMPLE 5

Determination of cAMP Content

After drug treatment of monolayer cultures in 60 mm dishes, 150 μl of water containing 4 mM EDTA was added to each dish. The cells were scraped, and the samples were stored at −20° C. until assay. The samples were thawed then sonicated for 20 sec at a power setting of 2 (Sonifier 450; Branson, Danbury, Conn.). A 15 μl aliquot was used for protein assay, and the rest of sample was heated for three min in boiling water bath. After centrifugation the supernatant was used for cAMP assay. Fifty μl of each diluted sample was added to a microtube in duplicate. Fifty μl of the labelled cAMP and 100 μl of the binding protein, purified bovine muscle, were added in each tube in this order. After vortex mixing for 5 sec, the sample in the ice bath was placed into a cold room at 2°–4° C. After 2 h-incubation, 100 μl of the charcoal suspension was added and the tubes were centrifuged immediately after vortex mixing. A 200 μl aliquot of supernatant was placed in a scintillation vial for counting with a beta counter. The standard curve was constructed using adenosine 3',5'-cyclic phosphate.

EXAMPLE 6

Effect of TPA on Cellular cAMP Content

The cytotoxicity of DDP can be increased by elevating the cAMP level, indicating that protein kinase A activity is a determinant of DDP sensitivity (Mann, et al., *Proc. Am. Assoc. Cancer Res.* 30:466 (1989)). To determine whether TPA was enhancing sensitivity via this mechanism, cellular cAMP levels were determined at 10 and 60 min following the start of exposure to 0.1 μM TPA. Forskolin, a potent activator of adenylate cyclase (Seamon, *ISI Atlas Sci. Pharmacol.* 250–253 (1987)), was included as a positive control. The results are shown on Table 4.

TABLE 4

Effect of TPA and Forskolin on cAMP levels

| Treatment | Duration of Treatment | |
|---|---|---|
| | 10 min. mean ± SD[a] | 60 min. mean ± SD[a] |
| No Treatment | 1.9 ± 1.9[b] | 21.4 ± 10.8[b] |
| Acetone | 0.8 ± 1.2[b] | 12.6 ± 6.0[b] |
| TPA | 2.7 ± 1.0[b] | 8.2 ± 2.9[b] |
| Forskolin | 2135.0 ± 305[b] | 6365.0 ± 635[b] |

[a]pmol/mg protein, values are means of 6 experiments.
[b]significantly different from the corresponding value for forskolin at the p > 0.01 level as determined by the t-test on grouped data.

The data presented in Table 4 shows that the acetone vehicle control reduced cAMP content to 59% of the untreated control. TPA reduced the cAMP level to 38% of the untreated control or 65% of the vehicle control at 60 min. In contrast, forskolin increased the cAMP content by 297-fold. Although the biologic significance of the TPA-induced reduction in cAMP level is not clear, TPA clearly did not increase cAMP levels into the range associated with forskolin-induced enhancement of DDP sensitivity.

EXAMPLE 7

Effect of Phorbol on DDP Sensitivity

Figure 8:
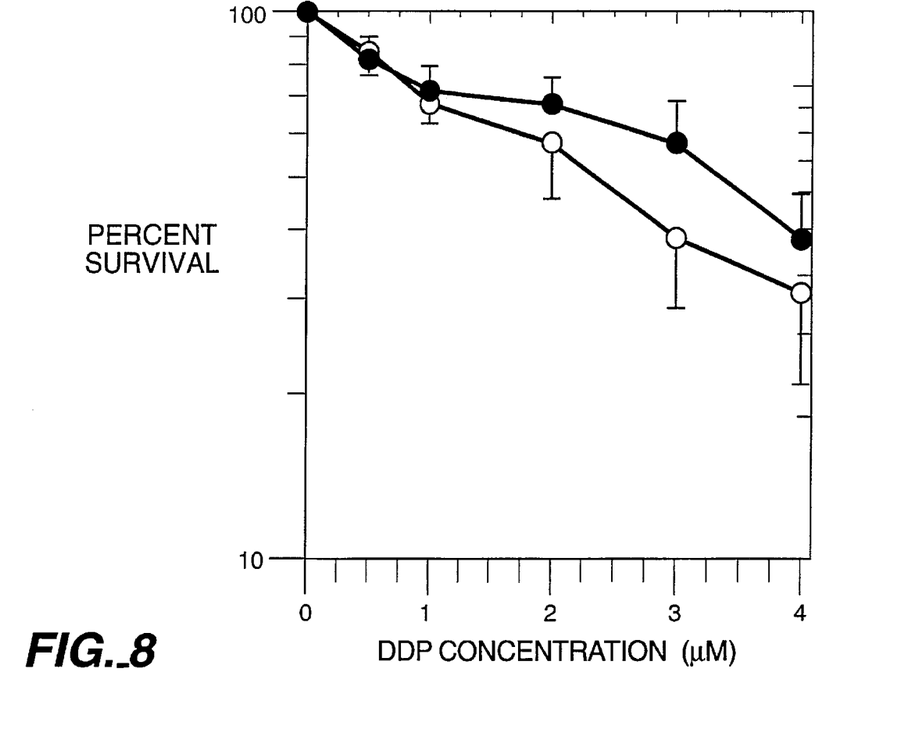
FIG. 8 demonstrates the effect of phorbol on DDP sensitivity.

The results presented above suggested that protein kinase C may be involved in regulating DDP sensitivity. To test this further, cells were treated with phorbol, a compound that has structural homology to TPA but not to diacylglycerol, and is known to be inactive as a tumor promoter and activator of protein kinase C. FIG. 8 demonstrates the effect of phorbol on DDP sensitivity. Cells were treated with appropriate concentrations of DDP in the presence (●) or absence (○) of 10$^7$M phorbol for 1-h. Drug cytotoxicity was determined by colonogenic assay on plastic dishes. Points, mean values of three experiments performed with triplicate cultures; bars, S.D. As shown in FIG. 8, phorbol failed to enhance DDP sensitivity, and, in fact slightly reduced it.

EXAMPLE 8

Effect of Protein Kinase C Inhibitors on TPA Enhancement of DDP Sensitivity

Staurosporine was used as a potent inhibitor of protein kinase C activity (Tamaki, et al., *Biochem. Biophys. Res. Commun.* 135:397–402 (1986)). 2008 cells were treated with TPA and DDP either in the presence or absence of 5 pM staurosporine for 1 h. 2008 cells trypsinized from monolayer culture were adjusted to a concentration of 6000 cells per 5 μl in a tissue culture tube (Corning Glass Works, Corning, N.Y.). Five μl of staurosporine (STS) solution was added to each tube to produce a final concentration of 5 nM. Control tubes received water alone. Tubes were preincubated in humidified 5% $CO_2$ in air for 1 h, followed by another 1 h incubation with or without 2 μM DDP and/or 10$^7$M TPA. Each tube was then centrifuged and the cells were resuspended in 15 ml of complete medium and used for colony assay. Cloning efficacy under these conditions was 10%.

Figure 9:
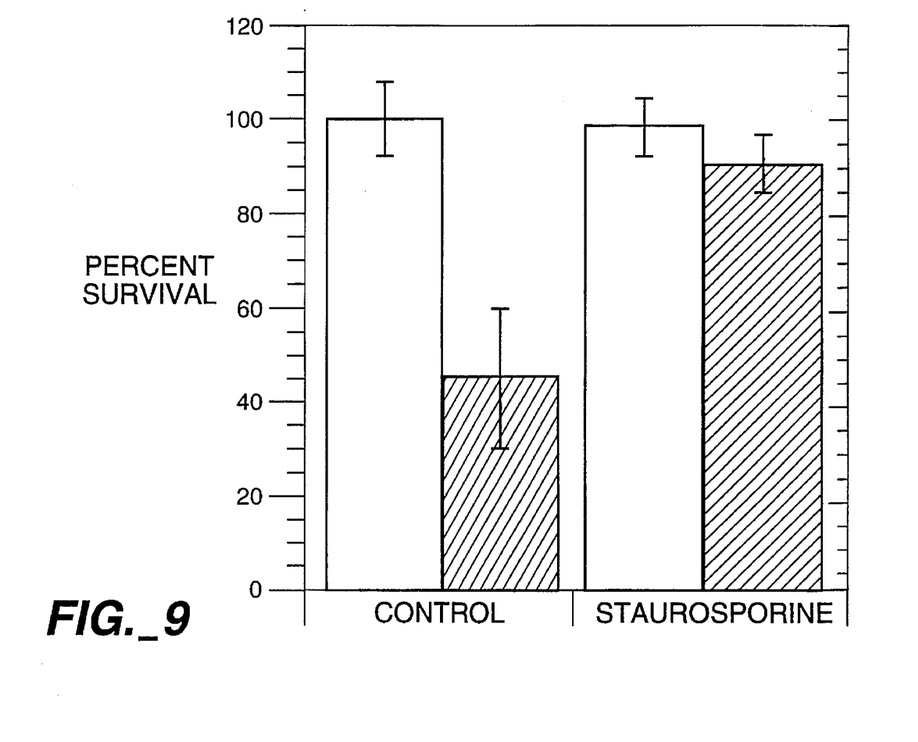
FIG. 9 demonstrates the effects of STS on the sensitivity of 2008 cells to TPA.

DDP (2 μM) alone reduced survival to 85±5% of control, whereas the addition of 0.1 μM TPA enhanced sensitivity, reducing survival to 38±16% of control. FIG. 9 demonstrates the effects of staurosporine on the sensitivity of 2008 cells to TPA. After a 1 h preincubation in medium containing (STS) or lacking (Control) 5 nM STS, cells were treated with 2 μM DDP in the presence (B) or absence (A) of $10^7$M TPA for 1 h. DDP cytotoxicity was determined by colonogenic assay on plastic dishes. Columns, mean values of three experiments performed with triplicate cultures; bars, S.D. In FIG. 9, these data have been normalized such that the survival with 2 μM DDP alone is 100%, and the addition of TPA reduced survival to 44%. When the cells were pretreated with staurosporine, the effect of TPA was completely blocked, and survival in the presence of all three agents were 96% of that produced by DDP alone. Control experiments showed that staurosporine by itself did not enhance or inhibit sensitivity to DDP. These data strongly suggest that TPA sensitization is mediated by protein kinase C (pkC).

EXAMPLE 9

Enhancement of Sensitivity in DDP-resistant Cells

Figure 10:
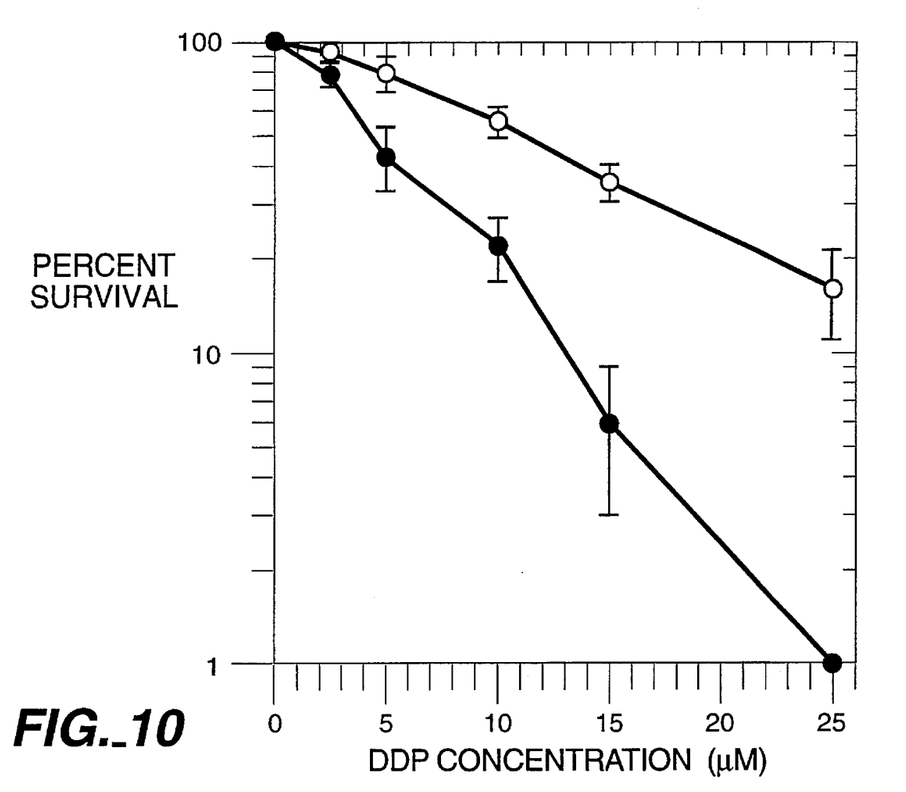
FIG. 10 demonstrates the TPA effect on the DDP sensitivity of DDP-resistant cells.

The 2008/C13*5 cell line is 8–10-fold resistant to DDP. FIG. 10 demonstrates the effect of TPA on the DDP sensitivity ofoDDP-resistant cells. C13*5 cells were treated with appropriate concentration of DDP in the presence (●) or absence (0) of $10^{-7}$M TPA for 1 h. Drug cytotoxicity was determined by colonogenic assay on plastic dishes. Each point represents the mean values of 3 experiments performed with triplicate cultures. The bars represent the standard deviation. FIG. 10 shows that when these cells were exposed for 1 h concurrently to TPA and DDP, the $IC_{50}$ was reduced from 13.1±2.7 μM (S.D.) to 4.9±1.4 μM (S.D.). This 2.6-fold sensitization was nearly identical with the 2.5 fold sensitization observed in the DDP-sensitive 2008 cells. At the end of a 1-h incubation, the DDP-resistant 2008/C13*5 cells had accumulated 37.0±3 pmol/mg of protein in cells treated with medium alone, 38.7± to DDP. In order to assess the effect of protein synthesis on the sensitization process, cycloheximide (CHM) was used to inhibit protein synthesis (Wilkinson, and MacLeod, *EMBO J.* 7:101–109 (1988)). Cells were incubated first with CHM 5 μg/ml for 10 minutes, then with 2 μM DDP alone or with $10^{-7}$M TPA for 1 h in serum free medium prior to plating in regular medium for colony formation.

TPA reduced survival to 33±5% (S.D.) of control in the absence of CHM, and 41±7% (S.D.) of controls in the presence of CHM. Thus, induction of DDP sensitivity was neither blocked nor augmented by CHM, suggesting that TPA-induced changes occurred in the absence of protein synthesis.

The data presented herein provide four lines of evidence arguing that protein kinase C is involved in the regulation of DDP sensitivity. First, TPA produced a consistent increase in DDP sensitivity under conditions where, even at a 10-fold higher concentration, it was totally nontoxic. Although TPA may do other things as well, the major effect by which it mediates changes in cell phenotype appears to be through the activation of protein kinase C. Second, phorbol, an inactive analog of TPA, was unable to enhance DDP sensitivity. Third, the TPA-induced increase in DDP sensitivity was completely blocked by pretreatment of the cells with staurosporine for 1 h. Fourth, the time course of sensitization is consistent with the expected time course for activation or inactivation of protein kinase C following a 1-h TPA exposure. Enhancement was apparent after a 1-h concurrent exposure, was maximal 2 h from the start of TPA exposure, and had disappeared by 7 h. Taken together, these results provide very strong evidence for the involvement of protein kinase C.

Prolonged exposure of cells to TPA produces down regulation of protein kinase C activity in a variety of cell systems, and if it is stimulation of protein kinase C activity that accounts for enhanced DDP sensitivity, one might have expected a 24-h exposure to TPA to reduce sensitivity. Instead, a 24-h exposure to TPA produced exactly the same degree of enhancement as a 1-h exposure. Protein kinase C activity was not measured at the end of the 24-h exposure, and it is possible that the enzyme was not down regulated in these cells as occurs also in KB cells. The protein(s) phosphorylated by protein kinase C that transmit the signal for enhanced DDP sensitivity is not known. The activation of adenyl cyclase with forskolin, or elevation of cAMP with dibutyl cAMP, enhances sensitivity to DDP in a synergistic manner. Weiner and Scarpa (Weiner and Scarpa, *J. Biol. Chem.* 264:4324–4326 (1989)) reported that TPA could potentiate the forskolin-induced cAMP response, and Plet et al, (Plet, et al., *Cancer Res.* 48:3993–3997 (1988)) showed that TPA increased protein kinase C activity. However, several lines of evidence argue against involvement of protein kinase A in the TPA-mediated enhancement of DDP sensitivity. First, direct measurement of cAMP showed no change when cells were treated with TPA. Second, activation of protein kinase A by forskolin is associated with enhanced of DDP uptake into the cell, an effect not produced by TPA. Third, TPA was equally effective in the DDP-sensitive 2008 cells and the DDP-resistant 2008/C13*5 cells. In contrast, the ability of forskolin to enhance DDP sensitivity is markedly blunted in 2008/C13*5 cells compared to the 2008 cells. These points also argue for the involvement of two separate protein kineses in the regulation of DDP sensitivity.

TPA enhancement of DDP sensitivity was associated with no change in cellular DDP accumulation. Since the cytotoxicity of DDP is believed to be related to the extent of DNA intrastrand, interstrand, and DNA protein cross-link formation, the results suggest that intracellular drug is more effective at platinating DNA following TPA treatment. Three mechanisms of DDP resistance have been identified which can participate in this decrease conjugation with glutathione, decreased binding to metallothioneins, or decreased DNA repair. The human metallothionein II gene is one of the TPA-inducible genes (Angel, et al., *Cell* 49:729–739 (1987); Lee, et al., *Cell* 49:741–522 (1987)), and, in contrast to what was observed, an increase in the transcription rate of the metallothionein II gene might be expected to result in DDP resistance. TPA might down regulate metallothionein in these cells, but the cellular half-life of metallothioneins is long and inconsistent with the time course of TPA induced DDP sensitization. However, one might postulate that TPA is altering the ability of metallothioneins to bind DDP, glutathione levels, glutathione-S-transferase activity, or DNA repair activity. The fact that the TPA effect was equivalent in DDP-sensitive and resistant cells indicates that selection for DDP resistance did not produce any lesions in the TPA signal transduction pathway involved in this sensitization. The signal pathway remains fully intact in both types of cells, indicating that the changes that account for DDP resistance involves biochemical steps distinct from those that participate in the TPA signal transduction pathway.

Administration of the compounds useful in the method of the present invention may be by topical, parenteral, oral, intranasal, intravenous, intramuscular, subcutaneous, or any other suitable means. The dosage administered may be dependent upon the age, weight, kind of concurrent treatment, if any, and nature of the condition being treated. The effective compound useful in the method of the present invention may be employed in such forms as capsules, liquid solutions, suspensions, or elixirs, for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the method of the present invention.

The term "individual" is meant to include any animal, preferably a mammal, and most preferably a cat, dog, cow or human.

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary, and are not intended as limitations on the scope of the present invention. Changes therein and other uses will occur to those skilled in the art which are encompassed within the spirit of the invention and are defined by the scope of the appended claims.

What is claimed is:

1. A method of enhancing the toxicity of taxol in human ovarian carcinoma cells consisting of administering to individuals in need thereof an effective amount of taxol and an effective amount of epidermal growth factor.

* * * * *